(12) United States Patent
Simmler et al.

(10) Patent No.: US 9,012,414 B2
(45) Date of Patent: Apr. 21, 2015

(54) COSMETIC COMPOSITION

(75) Inventors: Charlotte Simmler, Sélestat (FR);
Virginie Leplanquais, Fay-aux-Loges (FR); Emmanuelle Noblesse, Donnery (FR); Patrice Andre, Neuvill aux Bois (FR); Annelise Lobstein, Lipsheim (FR)

(73) Assignees: Guerlain, Paris (FR); Universite de Strasbourg, Strasbourg (FR); Centre National de la Recherche Scientifique, Paris (FR)

( * ) Notice: Subject to any disclaimer, the term of this patent is extended or adjusted under 35 U.S.C. 154(b) by 201 days.

(21) Appl. No.: 13/639,997

(22) PCT Filed: Apr. 14, 2011

(86) PCT No.: PCT/IB2011/051628
§ 371 (c)(1),
(2), (4) Date: Mar. 5, 2013

(87) PCT Pub. No.: WO2011/125057
PCT Pub. Date: Oct. 13, 2011

(65) Prior Publication Data
US 2013/0157968 A1  Jun. 20, 2013

(30) Foreign Application Priority Data
Apr. 9, 2010 (FR) .................... 10 52719

(51) Int. Cl.
| | |
|---|---|
| A61K 31/7034 | (2006.01) |
| A61K 8/60 | (2006.01) |
| A61K 8/49 | (2006.01) |
| A61Q 19/08 | (2006.01) |
| C07H 15/203 | (2006.01) |
| C07H 1/08 | (2006.01) |
| C07H 15/207 | (2006.01) |

(52) U.S. Cl.
CPC ............... *A61K 8/602* (2013.01); *A61K 8/498* (2013.01); *A61K 31/7034* (2013.01); *A61Q 19/08* (2013.01); *C07H 15/203* (2013.01); *C07H 1/08* (2013.01); *C07H 15/207* (2013.01)

(58) Field of Classification Search
None
See application file for complete search history.

(56) References Cited

U.S. PATENT DOCUMENTS

2009/0238848 A1* 9/2009 Andre et al. ............ 424/401
2011/0002968 A1* 1/2011 Leplanquais et al. ...... 424/401

FOREIGN PATENT DOCUMENTS

FR  2 924 348 A1  6/2009

OTHER PUBLICATIONS

Mohammad Najmul Ghani Khan, Khazaain-al-Advia, vol. 1 (20th century AD), Nadeem Yunus Printer/Sheikh Mohd Basheer & Sons, Lahore India, 1911, p. 839.
English Translation of: Mohammad Najmul Ghani Khan, Khazaain-al-Advia, vol. 1 (20th Century AD), Nadeem Yunus Printer/Sheikh Mohd Basheer & Sons, Lahore India, 1911, p. 839.

* cited by examiner

*Primary Examiner* — Traviss C McIntosh, III
(74) *Attorney, Agent, or Firm* — Arent Fox LLP

(57) ABSTRACT

The invention relates to novel eucomic acid (2-(4-hydroxybenzyl)malic acid) derivatives or plant extracts comprising such derivatives, and also to cosmetic or dermatological compositions containing these compounds or these extracts, and to cosmetic care methods using said compositions. Exemplary compounds are represented by formula (I) below:

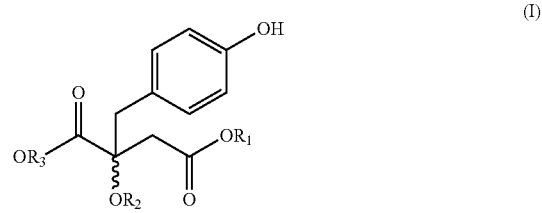

in which, with the proviso that $R_1$, $R_2$ and $R_3$ are not simultaneously a hydrogen atom, $R_1$ and $R_3$ each independently represent a hydrogen atom or a saturated or unsaturated, preferably $C_1$-$C_{12}$, hydrocarbon-based chain comprising an aromatic group, preferably a phenyl, said aromatic group being preferably substituted with a group comprising a sugar, preferably a monosaccharide or disaccharide, said chain optionally also comprising one or more heteroatoms preferably chosen from O, S and N, and $R_2$ represents a hydrogen atom or a sugar, preferably a monosaccharide or disaccharide, said sugar being optionally substituted, in particular with a residue comprising a saturated or unsaturated, preferably $C_1$-$C_{12}$, hydrocarbon-based chain itself comprising an aromatic group, preferably a phenyl, said hydrocarbon-based chain optionally also comprising one or more heteroatoms preferably chosen from O, S and N.

5 Claims, 10 Drawing Sheets

Measurement of desmoglein 1 expression

Untreated control

Positive control = 3% Vitactyl Clair

VT1 - 12 µg/ml

VT2 - 12 µg/ml

VT3 - 12 µg/ml

COSMETIC COMPOSITION

CROSS-REFERENCE TO RELATED APPLICATION

This application is a National Stage entry of International Application No. PCT/IB2011/051628 filed Apr. 14, 2011, which claims priority to French Patent Application No. 1052719 filed Apr. 9, 2010, the disclosure of the prior applications are hereby incorporated in their entirety by reference.

The invention relates to novel eucomic acid (2-(4-hydroxybenzyl)malic acid) derivatives, cosmetic or dermatological compositions comprising at least one of these compounds and care methods using said compositions.

PRIOR ART

Mitochondria constitute the factory for producing cell energy, by virtue of their respiratory chain and oxidative phosphorylation. During skin aging, in particular photo-induced skin aging, a decrease in mitochondrial functions is observed.

As a general rule, a defective mitochondrial respiratory chain results in an intracellular increase in reactive oxygen species (ROSs), which accelerates the skin aging process. This mitochondrial dysfunction is responsible for a decrease in cell energy metabolism which in the end compromises cell energy production. In the cosmetics industry, active agents capable of stimulating the functioning of the mitochondrial respiratory chain, and thus of activating cell energy metabolism, claim anti-aging functions (CoQ10, Resveratrol). Moreover, cosmetic active agents which stimulate cell renewal and therefore differentiation contribute to maintaining a young healthy skin.

The present invention relates to novel compounds derived from eucomic acid (2-(4-hydroxybenzyl)malic acid), in particular obtained from an extract of the orchid *Papilionanthe teres*, which have such properties.

Eucomic acid is known. It was first of all isolated from an extract of *Eucomis punctata* (family Liliaceae) bulbs (Heller et al., *Helvetica Chimica Acta*, 1984, 57 (6), 1766-84), and then subsequently identified in other plant species such as *Lotus japonicus* (Fabaceae), *Crotalaria sessifiora* (Fabaceae), *Crataegus pinnatifada* (Rosaceae), or alternatively *Encyclia michuacana* (Orchidaceae).

The family Orchidaceae (orchidaceans or orchids) is a very large family of monocotyledonous plants. It is the most diversified plant family, containing more than twenty-five thousand species, distributed through eight hundred and fifty genera. A certain number of orchids have already been the subject of studies in the cosmetics field, aimed at applications for skincare.

For example, patent application FR 2 924 348 discloses an extract obtained from at least one part of the orchid *Vanda teres*, now classified in the *Papilionanthe* genus as the species called *Papilionanthe teres*, and also the use of said extract as an active agent in a cosmetic composition comprising at least one cosmetically acceptable excipient, and intended to be applied to the skin in order to reduce or delay the effects of skin aging.

This *Papilionanthe teres* extract is therefore particularly advantageous from the point of view of its activities, in particular cosmetic and dermatological activities. However, to the inventors' knowledge, no molecule responsible for these activities has, to date, either been isolated or identified.

PURPOSES OF THE INVENTION

The main purpose of the present invention is to provide novel chemical compounds that can be used as cosmetic or dermatological active agents capable of reducing or delaying the effects of skin aging, and/or of maintaining or improving skin moisturization and/or promoting skin healing.

The purpose of the present invention is also to provide these novel compounds in a form that can be used as an active agent in a cosmetic or dermatological composition, in particular in the form of plant extracts enriched in at least one of these novel compounds.

According to another aspect, the invention relates to a cosmetic or dermatological composition containing at least one of these compounds as a cosmetic or dermatological agent, or such an active agent in the form of a plant extract, in a cosmetically or dermatologically acceptable vehicle, compatible with topical application to the skin.

The purpose of the invention is also to solve the technical problem consisting of the isolation and characterization of one or more active molecules of an extract of the orchid *Papilionanthe teres*.

Finally, the purpose of the invention is to propose a solution to these technical problems in a particularly simple and relatively inexpensive manner that can be used on the industrial and cosmetic level.

DETAILED DESCRIPTION OF THE INVENTION

The inventors of the present invention have isolated and identified novel compounds derived from eucomic acid, obtained in particular from an extract of the orchid *Papilionanthe teres*. These novel compounds, of formula (I) below, are collectively called "vandaterosides" in the present application (abbreviated to "VT").

The inventors have also demonstrated the impact of the vandaterosides of the invention on the functioning of the mitochondrial respiratory chain of human keratinocytes (NHK and HaCaT), focusing more specifically on respiratory chain complexes I and II and also on cytochrome C oxidase. They have also demonstrated that they significantly stimulate the functioning of the mitochondrial respiratory chain and the cell differentiation of human keratinocytes. These molecules therefore act at the heart of the regulation of energy metabolism and of the regulation of cellular oxidative stress and therefore are of unexpected interest as active agents in cosmetic or dermatological compositions for combating skin aging. By stimulating cell renewal and differentiation, the compounds participate in the cell metabolism and stimulate the renewal of the stratum corneum and contribute to maintaining a young healthy skin.

The techniques used call for, firstly, the measurement of the conversion of XTT (2,3-bis(2-methoxy-4-nitro-5-sulfophenyl)-5-[(phenylamino)carbonyl]-2H-tetrazolium hydroxide) to soluble formazan by NHK complexes I and II and, secondly, the actual measurement of the enzymatic activity of cytochrome C oxidase extracted from the mitochondria of human keratinocytes that have been modified (HaCaT).

Similarly, the inventors have evaluated the action of these vandaterosides on the production of NHK differentiation expression proteins (transglutaminase, involucrin, desmoglein I), by immunolabeling. This differentiation process participates in the cell renewal of the cornified envelope.

A first subject of the invention is directed toward a compound of formula (I),

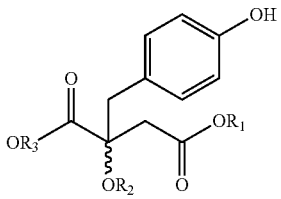

in which:

with the proviso that $R_1$, $R_2$ and $R_3$ are not simultaneously a hydrogen atom, $R_1$ and $R_3$ each independently represent a hydrogen atom or a saturated or unsaturated, preferably $C_1$-$C_{12}$, hydrocarbon-based chain comprising an aromatic group, preferably a phenyl, said aromatic group preferably being substituted with a group comprising a sugar, preferably a monosaccharide or disaccharide, said chain optionally also comprising one or more heteroatoms preferably chosen from O, S and N, and $R_2$ represents a hydrogen atom or a sugar, preferably a monosaccharide or disaccharide, said sugar being optionally substituted, preferably by esterification of one of the hydroxyl functions, in particular with a residue comprising a saturated or unsaturated, preferably $C_1$-$C_{12}$, hydrocarbon-based chain itself comprising an aromatic group, preferably a phenyl, said hydrocarbon-based chain optionally also comprising one or more heteroatoms preferably chosen from O, S and N.

The sugar is preferably a monosaccharide such as, for example, glucose, mannose, fructose, xylose or arabinose, or a disaccharide such as, for example, sucrose or maltose, or a derivative thereof.

Preferred compounds of the invention are in particular those of formula (I) in which $R_1$ and/or $R_3$ represent a benzyl group substituted with an $OR_4$ group, preferably in the para-position, in which group $R_4$ represents a group chosen from (i) a hydrogen atom or an alkyl group comprising a linear or branched, and/or cyclic, aromatic or nonaromatic, saturated or unsaturated, preferably $C_1$-$C_{12}$, hydrocarbon-based chain optionally comprising one or more heteroatoms preferably chosen from O, S and N, said carbon-based chain being itself unsubstituted or substituted, preferably with a group comprising a sugar, preferably a monosaccharide or disaccharide; and (ii) a residue of a sugar, preferably a monosaccharide or disaccharide, said sugar being optionally substituted, in particular with a residue comprising a linear or branched, and/or cyclic, aromatic or nonaromatic, saturated or unsaturated, substituted or unsubstituted, preferably $C_1$-$C_{12}$, hydrocarbon-based chain itself optionally comprising one or more heteroatoms preferably chosen from O, S and N.

Preferably, $R_1$ and $R_3$ are identical or different and represent a hydrogen atom or a benzyl group preferably substituted with a glucopyranosyloxy group, such as the 4-β-D-glucopyranosyloxybenzyl group, and $R_2$ represents a glucopyranosyl group, such as the β-D-glucopyranosyl group, preferably substituted, in particular by esterification of a hydroxyl function, with a saturated or unsaturated, preferably $C_1$-$C_{12}$, hydrocarbon-based chain itself comprising an aromatic group, preferably a phenyl, $R_2$ representing in particular the β-D-glucopyranosyl-3-trans-cinnamoyl ester group; $R_1$, $R_2$ and $R_3$ not being simultaneously a hydrogen atom.

Compounds which are more particularly preferred are those for which $R_1$ and/or $R_3$ are identical or different and represent a benzyl group substituted with an $OR_4$ group, $R_4$ representing a glucopyranosyl group, which is optionally substituted.

Among the latter compounds, the preferred compounds are in particular those for which, according to formula (I), $R_1$ and $R_3$ are identical and each represent a 4'-(glucopyranosyloxy) benzyl group.

Advantageously, the asymmetric carbon atom in position 2 of the malate part according to formula (I) is presented according to an (R) enantiomer conformation.

The compounds that are particularly preferred for implementing the invention are those which have the formulae below:

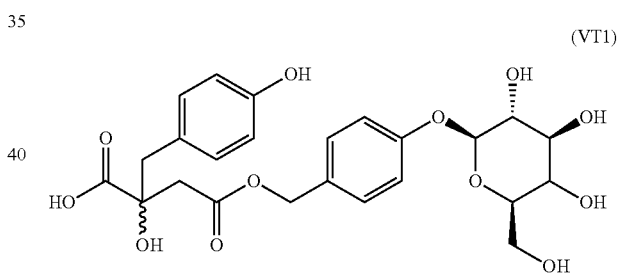

(VT1)

and in particular 4-(4-β-D-glucopyranosyloxybenzyl)-(2R)-2-(p-hydroxybenzyl) malate,

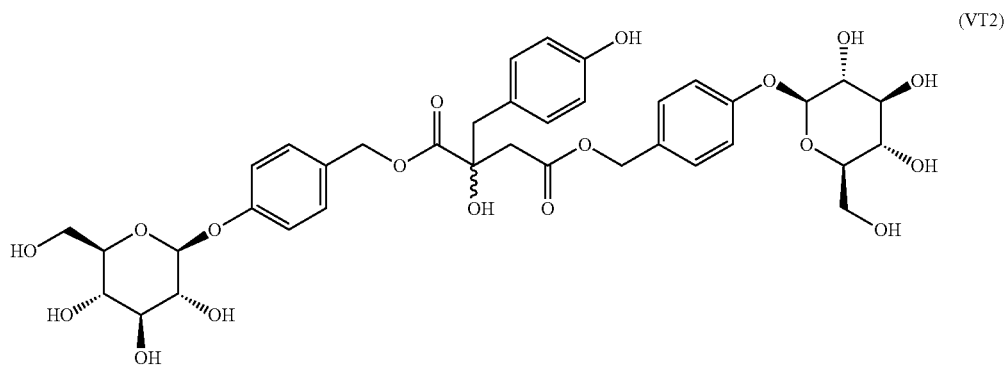 [SMILES: O=C(CC(O)(Cc1ccc(O)cc1)C(=O)OCc1ccc(O[C@@H]2O[C@H](CO)[C@@H](O)[C@H](O)[C@H]2O)cc1)OCc1ccc(O[C@@H]2O[C@H](CO)[C@@H](O)[C@H](O)[C@H]2O)cc1]

(VT2)

and in particular 1,4-bis(4-β-D-glucopyranosyloxybenzyl)-(2R)-2-(p-hydroxybenzyl) malate, that it comprises the VT3 compound at a content of greater than 8% by weight, relative to the weight of the dry extract,

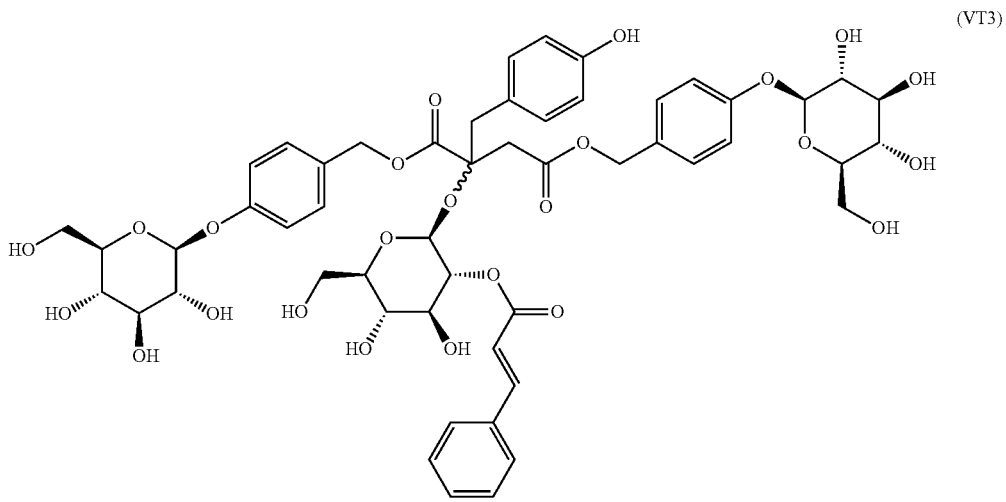 [SMILES: O=C(/C=C/c1ccccc1)O[C@H]1[C@H](OC(CC(=O)OCc2ccc(O[C@@H]3O[C@H](CO)[C@@H](O)[C@H](O)[C@H]3O)cc2)(Cc2ccc(O)cc2)C(=O)OCc2ccc(O[C@@H]3O[C@H](CO)[C@@H](O)[C@H](O)[C@H]3O)cc2)O[C@H](CO)[C@@H](O)[C@@H]1O]

(VT3)

and in particular 14-bis(4-β-D-glucopyranosyloxybenzyl)-(2R)-2-(2-β-D-glucopyranosyl-3-trans-cinnamoyl ester)-2-(p-hydroxybenzyl)malate.

A second subject of the invention relates to a plant extract characterized in that it is specifically enriched in one or more of the compounds of formula (I) as defined above.

Said extract is advantageously obtained from at least one part of an orchid, in particular of an orchid belonging to the *Papilionanthe, Vanda* or *Encyclia* genus.

A preferred extract is in particular characterized in that it is obtained from the orchid *Papilionanthe teres*, in particular from stems, roots or flowers of said orchid, and in that it comprises at least one compound of formula (I), and preferably VT1 and/or VT2 and/or VT3.

The term "specifically enriched" or "enriched" is intended to mean an extract which is obtained by means of a step aimed at intentionally increasing the content, in the extract, of compounds of formula (I), preferably of VT1 and/or VT2 and/or VT3 compound(s).

Said enriched extract is in particular advantageously obtained by means of a sugar removal step or by fractionation, and for example by size exclusion chromatography.

Typical extracts are those of which the dry extract comprises a concentration of compounds of formula (I), preferably of VT1 and/or VT2 and/or VT3 compound(s), which is greater than that of a dry extract obtained after extraction, without a step aimed at specifically increasing the concentration of the abovementioned compounds.

Preferably, said enriched extract comprises at least 40%, at least 50%, at least 60%, at least 70% and more preferably at least 80% by weight of compounds of formula (I), preferably of VT1 and/or VT2 and/or VT3 compound, relative to the total weight of the dry extract.

A particular extract of the invention, advantageously prepared from the orchid *Papilionanthe teres*, is characterized in that it comprises one or more compounds chosen from VT1 and/or VT2 at a cumulative content of greater than 40% by weight, relative to the weight of the dry extract, preferably greater than 60%, and more preferably greater than 80%.

Another extract of the invention, also advantageously prepared from the orchid *Papilionanthe teres*, is characterized in preferably greater than 15% by weight, preferably greater than 25% by weight, and more preferably greater than 40% by weight.

Advantageously, the extract of the invention is characterized in that it is made up of at least 80% by weight of the VT1, VT2 and VT3 compounds, relative to the total weight of the dry extract, preferably at least 90% by weight.

A preferred enriched extract is more particularly prepared from the stems or roots of the orchid *Papilionanthe teres*.

A third subject of the invention relates to a cosmetic or dermatological composition comprising, as cosmetic or dermatological active agent, at least one compound according to formula (I) and/or one plant extract comprising such a compound, advantageously according to any one of the variants and embodiments described above.

In addition to at least one of the abovementioned compounds or extracts, the cosmetic composition may also comprise one or more other cosmetic or dermatological active agents, in the form of purified molecules and/or of plant extracts, having cosmetic effects similar and/or complementary to those of said compounds.

The composition may thus in particular comprise one or more other plant extracts, obtained from whole plants or from parts of plants, or alternatively solutions prepared from extracts of these plants, the extracts being advantageously obtained by means of the methods conventionally used by those skilled in the art, and more particularly by extraction with a polar solvent or a mixture of polar solvents, advantageously chosen from water, $C_1$-$C_4$ alcohols or glycols.

The other cosmetic or dermatological active agents may be chosen, for example, from substances having an anti-aging activity; substances having a depigmenting activity or a lightening activity on the skin; substances having a slimming activity; substances having a moisturizing activity; substances having a calming, soothing or relaxing activity; substances which stimulate the microcirculation of the skin so as to improve the radiance of the complexion, in particular of the face; substances having a sebum-regulating activity for greasy skin care; substances intended to cleanse or purify the skin; and substances having a free-radical-scavenging activity.

The composition may advantageously comprise at least one extract of an orchid such as an orchid belonging to the *Brassocattleya* genus, for example an extract of the orchid *Brassocattleya marcella*, or to the *Encyclia* genus, for example an extract of the orchid *Encyclia michuacana*, or to the *Cattleya* genus, or to the *Vanda* genus, for example an extract of an orchid from *Vanda coerulea* or *Vanda denisoniana*, or else to the *Papilionanthe* genus.

Advantageously, the composition also comprises at least one cosmetically or dermatologically acceptable excipient which can in particular be chosen from pigments, colorants, polymers, surfactants, rheological agents, fragrances, electrolytes, pH adjusters, antioxidants and preservatives, and mixtures thereof.

The cosmetic or dermatological composition is advantageously in the form of a serum, a lotion, a cream or a hydrogel, in particular a mask, or else in the form of a stick or a patch.

A fourth subject of the invention relates to the use of at least one compound according to formula (I) or of at least one plant extract comprising such a compound, advantageously according to any one of the variants and embodiments described above, as a cosmetic or dermatological active agent in a cosmetic or dermatological composition.

Advantageously, said compound or said extract is an active agent intended for combating skin aging, in particular for reducing or delaying the effects of skin aging, restructuring the epidermis, firming the skin, and/or promoting the reduction or resorption of wrinkles and the protective properties of the epidermis, and/or for maintaining or improving skin moisturization and/or promoting skin healing.

The invention also relates to the use of at least one compound according to formula (I), or a plant extract comprising such a compound, advantageously according to any one of the variants and embodiments described above, as an active agent in a cosmetic or dermatological composition, said active agent stimulating the expression and/or the activity of mitochondrial dehydrogenases, and/or of cytochrome C oxidase, and/or of the mitochondrial respiratory chain, and/or cell energy metabolism and/or the differentiation and renewal of epithelial cells.

Advantageously, said active agent makes it possible to act on the epidermis, and in particular the epithelial cells, and even more particularly the keratinocytes.

The invention also relates to the use of at least one extract of the orchid *Papilionanthe teres*, in particular of stems or roots of the orchid *Papilionanthe teres*; comprising such a compound, advantageously according to any one of the variants and embodiments described above, as an active agent intended for combating skin aging, in particular for reducing or delaying the effects of skin aging, restructuring the epidermis, firming the skin, and/or promoting the reduction or resorption of wrinkles and the protective properties of the epidermis, and/or for maintaining or improving skin moisturization and/or promoting skin healing, in a cosmetic or dermatological composition, said active agent stimulating the expression and/or the activity of mitochondrial dehydrogenases, and/or of cytochrome C oxidase, and/or of the mitochondrial respiratory chain, and/or cell energy metabolism and/or the differentiation and renewal of epithelial cells.

Advantageously, the compounds of the invention are active agents for stimulating the expression of keratinocyte differentiation proteins.

For each of the subjects of the abovementioned invention, the concentration of compound of formula (I) or of extract comprising such a compound, used as cosmetic or dermatological active agent, in a cosmetic or dermatological composition, is between 0.0001% and 1% by weight, more particularly between 0.001% and 0.1% by weight, even better still between 0.01% and 0.1% by weight, relative to the weight of said composition.

The compositions of the invention exhibit a particularly desired effect for combating skin aging, in particular for reducing or delaying the effects of skin aging, restructuring the epidermis, firming the skin, and/or promoting the reduction or resorption of wrinkles and the protective properties of the epidermis, and/or for maintaining or improving skin moisturization and/or for promoting skin healing.

A subject of the invention is also a cosmetic or dermatological care method, characterized in that it comprises the application, to the areas of skin that are involved, of a cosmetic or dermatological composition as defined above, in an effective amount for combating skin aging, in particular for reducing or delaying the effects of skin aging, restructuring the epidermis, firming the skin, promoting the reduction or resorption of wrinkles and the protective properties of the epidermis, and/or for maintaining or improving skin moisturization and/or for promoting skin healing.

Advantageously, said method comprises the application of said composition to an area of skin of the face, of the neck or of the body, in particular of the hands, showing signs of aging, such as the presence of wrinkles or fine lines.

The present invention also relates to a method for preparing a compound of formula (I) according to the invention, or an enriched extract according to the invention, said method comprising a step of extracting at least one part of a plant, advantageously of an orchid, in particular of the orchid *Papilionanthe teres*, comprising such a compound, and at least one step of enriching the extract obtained in the extraction step, in one or more compounds of formula (I), and preferably in VT1 and/or VT2 and/or VT3 compounds.

Preferably, prior to the extraction step, this method comprises a step of grinding the whole plant or at least one part of the plant, preferably the stems, the leaves or the roots, and then a step of extracting this plant or the parts of said plant.

The plant or the parts of plants are advantageously dried or frozen before grinding.

Preferably, the extraction is carried out using at least one polar solvent. Among the polar solvents, use may be made of a single solvent or a mixture of solvents. The polar solvents used are preferably water; an alcohol, preferably a $C_1$-$C_4$ alcohol, and in particular methanol, ethanol or a propanol; a polyol, and in particular a glycol, and for example glycerol, propylene glycol or butylene glycol.

Among the mixtures of solvents, use is preferably made of an aqueous-alcoholic mixture, and preferably an ethanol/water mixture, and more particularly an ethanol/water mixture in a ratio of about 90/10 v/v.

The extraction can be carried out preferably in a polar solvent at reflux and preferably in a Soxhlet apparatus. It is possible to optimize the Soxhlet extraction by using solvents of increasing polarity, for instance with a succession of solvents of the alkane type (for example pentane, hexane, cyclopentane, cyclohexane, heptane, etc.), halogenated alkane type (for example dichloromethane), and then alcohol type (for example ethanol or methanol).

The extract can then be concentrated so as to eliminate the solvent or the mixture of solvents. It is therefore possible to obtain a dry compound, which can be solubilized or dispersed in a cosmetically or dermatologically acceptable excipient for final use in a composition of the invention.

The method of the invention advantageously comprises a step of enriching the extract obtained in the abovementioned extraction step, in one or more of the compounds of formula (I) as defined above. The method comprises in particular a step of enriching by removal of the sugars or by fractionation, and for example by size exclusion chromatography.

In addition, the extract can be partly or completely discolored, in particular in the presence of active carbon after having been placed in the presence of a polar solvent.

The extracted fractions can be purified by any method known to those skilled in the art, and for example by chromatography, in particular gel column chromatography, and/or high performance liquid chromatography (HPLC).

Other purposes, characteristics and advantages of the invention will become clearly apparent in the light of the explanatory description which follows, given with reference to examples of preparation of extracts and of tests demonstrating the properties of the extracts and to an example of a cosmetic composition using such extracts, given simply by way of illustration and which could not therefore in any way limit the scope of the invention.

In the examples, all the percentages are given by weight, the temperature is in degrees Celsius, and the pressure is atmospheric pressure, unless otherwise indicated.

Figure 6:
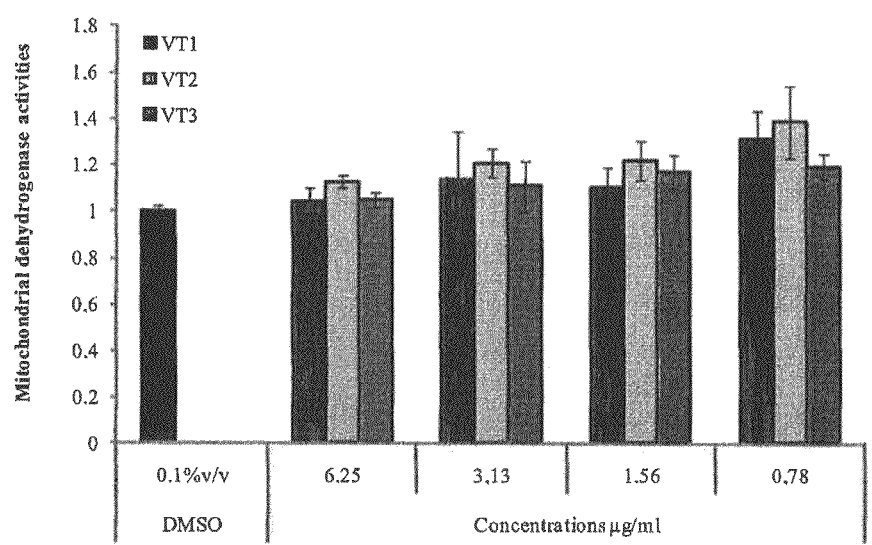

FIG. 6 represents the effect of the VT1, VT2 and VT3 compounds of the invention on the activation of mitochondrial dehydrogenases; Treatment time 48 h. Negative control DMSO (0.1%; v/v). Means±SD (standard deviation) calculated from three experiments.

Figure 7:
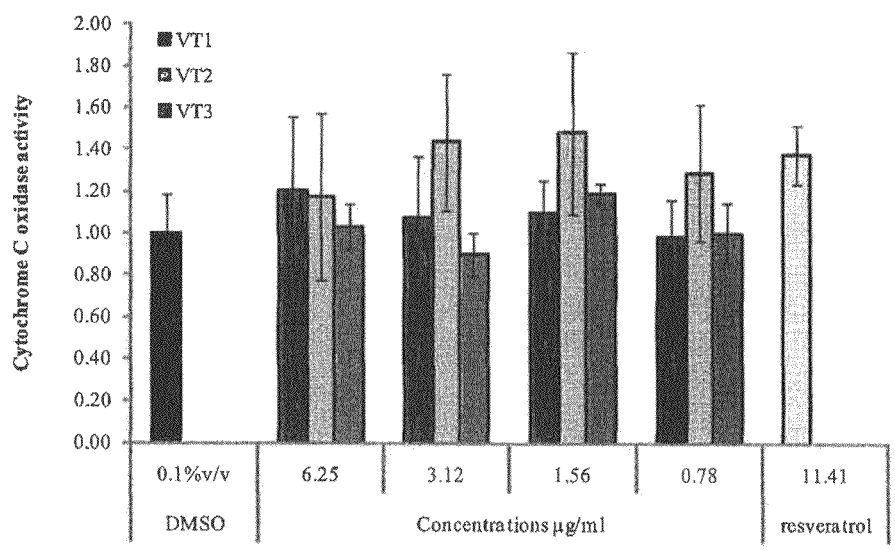

FIG. 7 represents the activity of the VT1, VT2 and VT3 compounds of the invention on the expression of cytochrome C oxidase; Treatment of HaCaT cells: 3 h. Negative control: untreated cells (DMSO (0.1%; v/v)), positive control: Resveratrol (11.41 µg/ml). Means±SD (standard deviation) obtained on three independent experiments.

Figure 8:
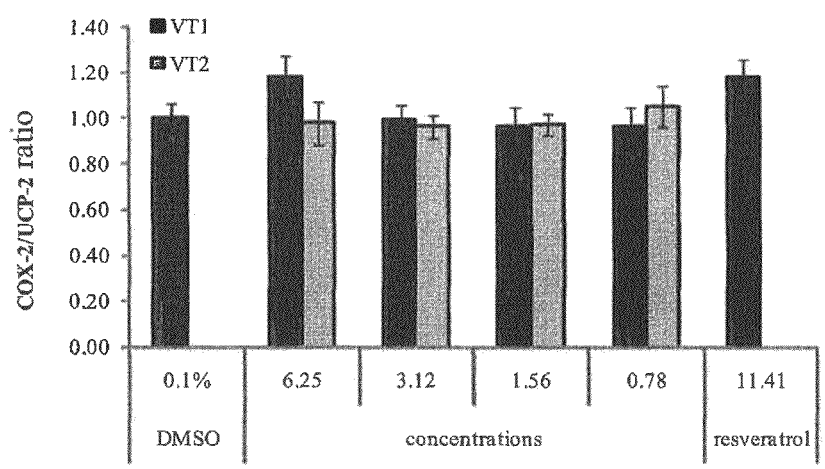

FIG. 8 represents the activity of the VT1, VT2 and VT3 compounds of the invention on mitochondrial biogenesis; Treatment of HaCaT cells: 48 h. Negative control: untreated cells (DMSO (0.1%; v/v)), positive control: Resveratrol (11.41 µg/ml). Means±SD (standard deviation) obtained on three independent experiments.

Figure 9:
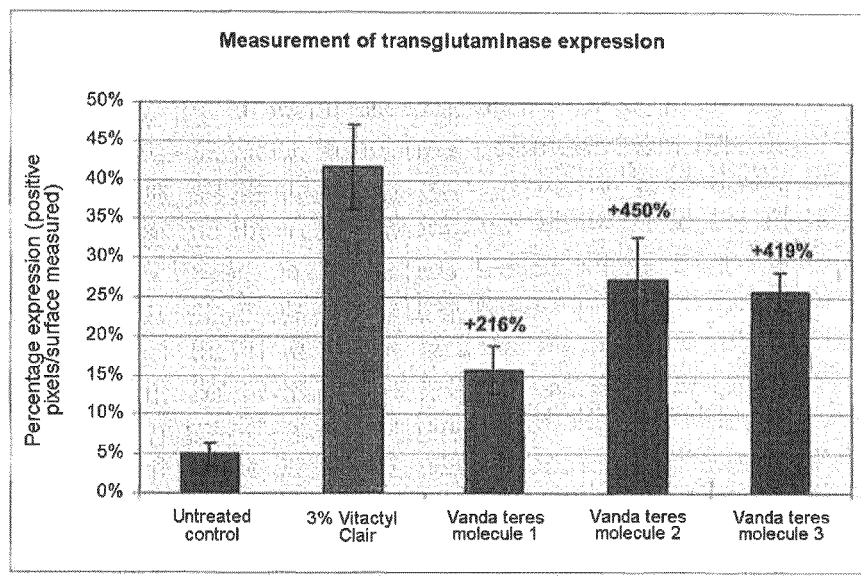
Figure 10:
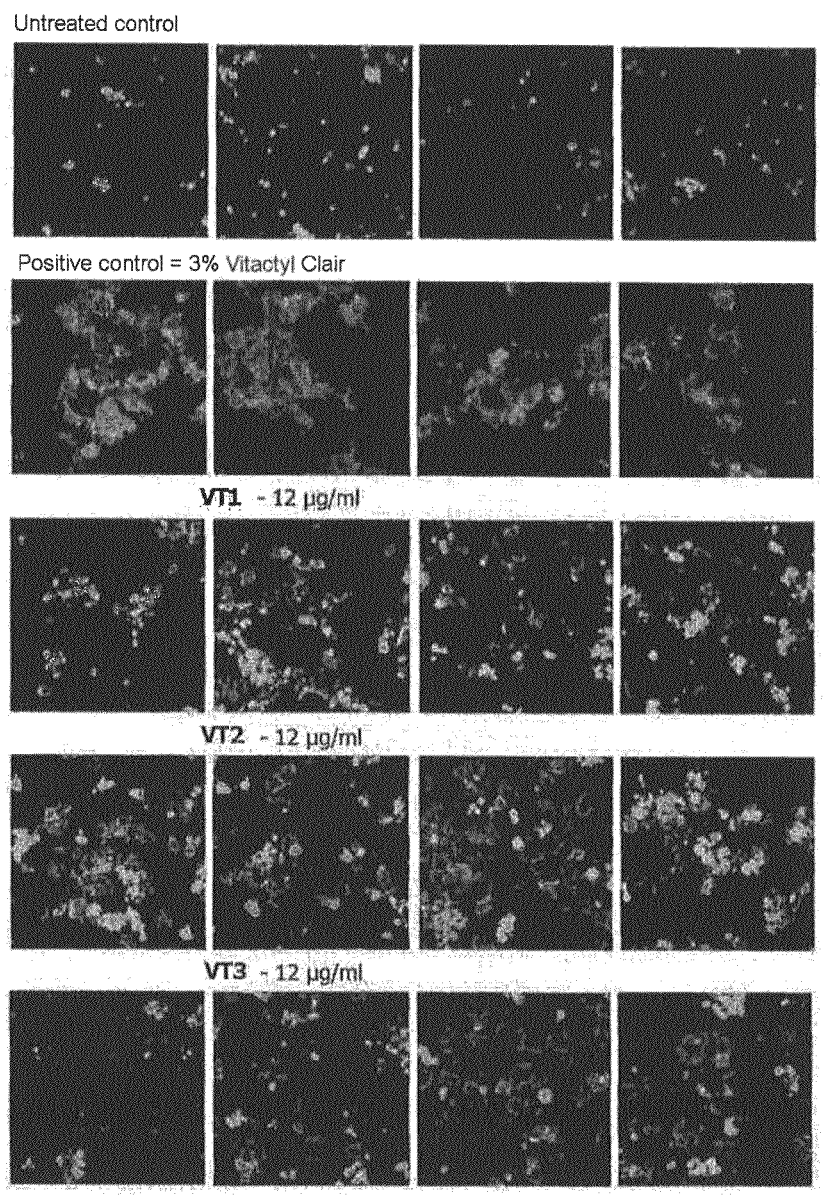
Figure 11:
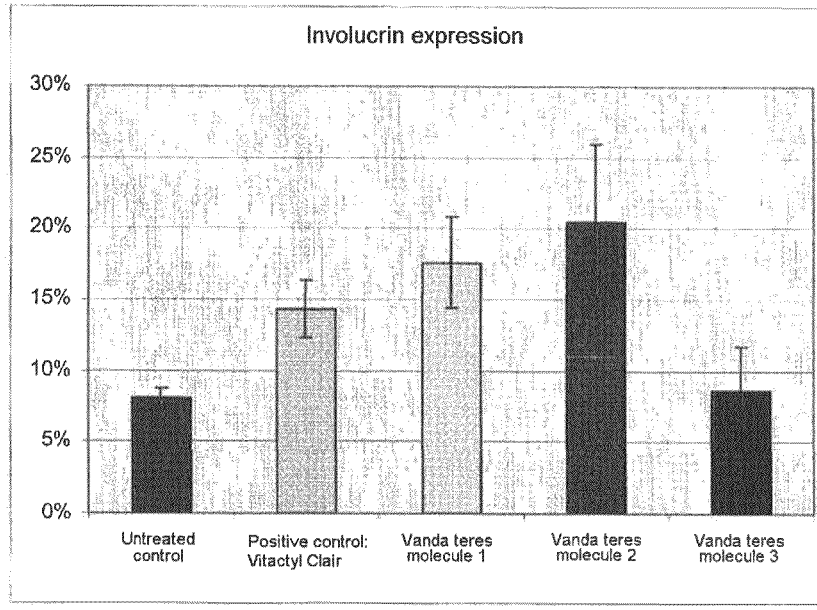
Figure 12:
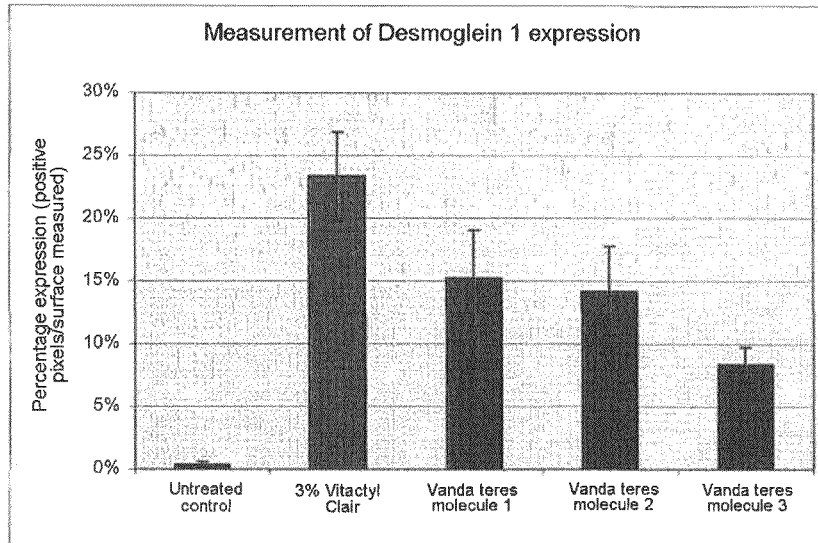
Figure 13:
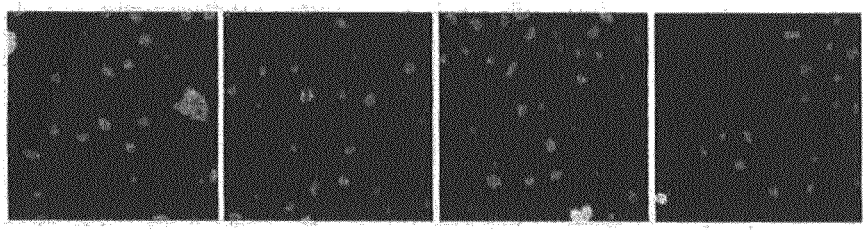
Figure 13:
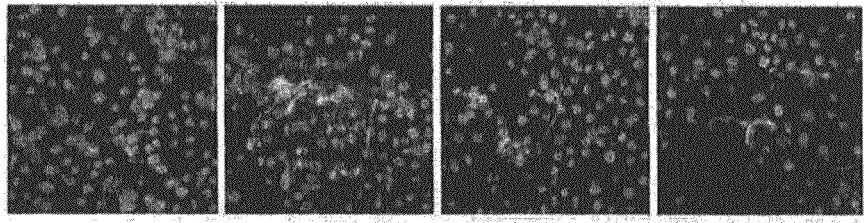
Figure 13:
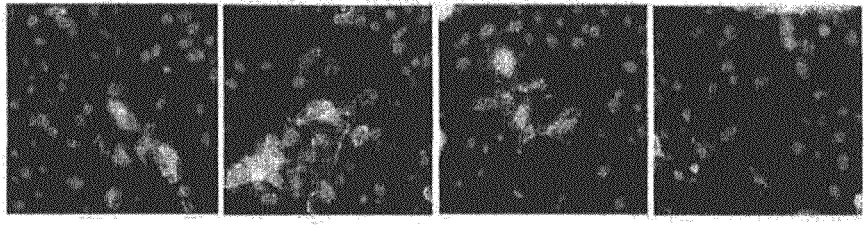
Figure 13:
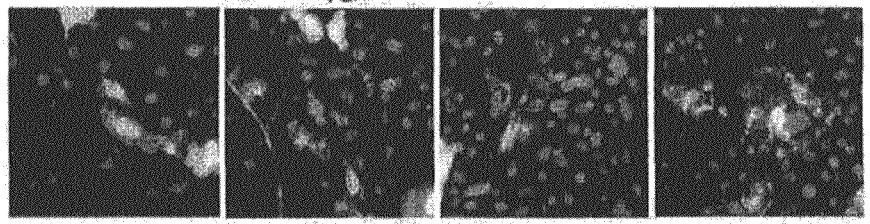
Figure 13:
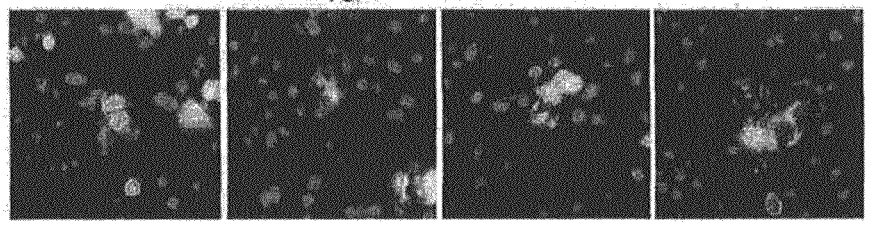

FIG. 9 represents the effect of treatment with the VT1, VT2 and VT3 compounds of the invention on transglutaminase expression;

FIG. 10 represents a photograph, taken on an electron microscope, of transglutaminase expression in the presence of the VT1, VT2 or VT3 compounds of the invention;

FIG. 11 represents the effect of treatment with the VT1, VT2 or VT3 compounds of the invention on involucrin expression;

FIG. 12 represents the effect of treatment with the VT1, VT2 or VT3 compounds of the invention on desmoglein 1 expression;

FIG. 13 represents a photograph, taken on an electron microscope, of the expression of desmoglein 1 in the presence of the VT1, VT2 or VT3 compounds of the invention.

EXAMPLE

Example 1

*Papilionanthe teres* Extracts

Various parts of the orchid *Papilionanthe teres* are analyzed in order to detect the presence of vandaterosides in each of these parts of the plant, and to determine the content thereof.

100 g of dry plant material (PM), consisting of the stems (example 1.1 and 1.2), roots (example 1.3) or leaves (example 1, 4) of the orchid *Papilionanthe teres* (origin Tian Zi, China), are ground before the extraction step.

Example 1.1

Aqueous-Alcoholic Extract of *Papilionanthe teres* Stems

A total aqueous-alcoholic extract of the dry PM (90/10 v/v ethanol (EtOH)/water, PM/solvent ratio: 1/15) is prepared at reflux (30 min, 80° C.). This total extract is obtained with a weight yield of 12.8% (weight of extract/weight of dry PM).

Example 1.2

Methanolic Extract of *Papilionanthe teres* Stems

A Soxhlet extraction (Soxtec Avanti 2055 apparatus), more specific than that of example 1.1, makes it possible to deplete the dry PM through the successive use of three solvents of increasing polarity: cyclohexane (45 min, 180° C.), dichloromethane (cycle 1: 45 min, 180° C., cycle 2: then 30 min, 180° C.) and methanol (MeOH) (2 cycles of 45 min, 180° C.).

This methanolic extract, which concentrates the vandaterosides, is obtained with a weight yield of 6.9% (weight of extract/weight of d PM).

Example 1.3

Aqueous-Alcoholic Extract of *Papilionanthe teres* Roots

A total aqueous-alcoholic extract is prepared according to the following conditions: 90/10 EtOH/water, using a PM/solvent ratio of 1/15. The extract is prepared at reflux (30 minutes, 80° C.). The weight yield obtained for the root extract is 14.8%.

Example 1.4

Aqueous-Alcoholic Extract of *Papilionanthe teres* Leaves

A total aqueous-alcoholic extract is prepared according to the following conditions: 90/10 EtOH/water, using a ground dry PM/solvent ratio of 1/15. The extract is prepared at reflux (30 minutes, 80° C.). The weight yield obtained is 15.0% for the leaf extract.

These extracts (examples 1.1 to 1.4) are analyzed according to the conditions described in example 2 (fractionation, isolation) in order to confirm the presence of 3 compounds of formula (I), respectively called VT1, VT2 and VT3 after isolation and structural elucidation. The respective concentrations thereof in the various extracts and fractions are determined by RP-HPLC according to the method of example 2.1, by external calibration: serial dilutions of each of the isolated compounds VT1, VT2 and VT3 are prepared in order to determine the calibration curve.

The results are indicated in table 1 below (see also FIG. 5):

TABLE 1 concentrations of the vandaterosides VT1, VT2 and VT3 in the various
*P. teres* extracts (% w/w means ± SD, injections in triplicate)

|  | VT1 | VT2 | VT3 |
|---|---|---|---|
| Aqueous-alcoholic extract of *P. teres* stems | 6.7 ± 1.7 | 14.1 ± 0.6 | 2.6 ± 0.2 |
| MeOH extract of *P. teres* stems | 9.4 ± 0.4 | 19.3 ± 1.2 | 3.4 ± 0.7 |
| Aqueous-alcoholic extract of *P. teres* leaves | 8.1 ± 0.6 | 13.4 ± 0.9 | 2.9 ± 0.0 |
| Aqueous-alcoholic extract of *P. teres* roots | 1.6 ± 0.4 | 24.8 ± 2.5 | 2.0 ± 0.0 |

Conclusions

It emerges from these analyses that:
- the vandaterosides VT1, VT2 and VT3 are present in all the parts of *Papilionanthe teres* plants (stems, leaves and roots);
- the extract of *Papilionanthe teres* roots concentrates VT2 at a content equal to 1.8 times that determined in the aqueous-alcoholic extracts of stems or leaves.

Example 2

Extracts Specifically Enriched in Vandaterosides

The extracts obtained according to example 1 above are selected in order to carry out a size fractionation step aimed at specifically enriching these extracts in compounds of formula (I), respectively called VT1, VT2 and VT3 after isolation and structural elucidation.

Example 2.1

Fractionation by Gel Column Chromatography

The fractionation of the methanolic extract obtained according to example 1.2. is carried out on a column of Sephadex LH 20 gel (LH20-100-Sigma) (28*180 mm) using a polar solvent gradient (transition from 100% water to 100% methanol, flow rate of 1 ml/min).

1 gram (g) of this methanolic extract is diluted in a water/methanol mixture (50/50 v/v) and deposited on 30 g of Sephadex gel. The polar molecules are separated according to their size and their solubility in the elution solvent.

20 fractions of 10 ml are obtained, and are combined according to their similar profiles obtained by thin layer chromatography (Eluent: ethyl acetate: acetic acid:formic acid: water (100:11:11:26 v/v/v/v, Support: 60 $F_{254}$ silica gel (0.25 mm, MERCK), Developer: Vanillin (Merck) —$H_2SO_4$ (97% Fluka) 5%) so as to in the end give ten fractions.

Reverse-Phase High Performance Liquid Chromatography (RP-HPLC) analyses aim to identify the fractions, among the ten starting fractions, which concentrate the compounds of formula (I) that are present in the total extract.

The RP-HPLC analysis is carried out using a chromatograph (Varian) that has a Nucleodur $C_{18}$ec column (5 μm, 250 mm×4.6 mm i.d.), equipped with a pump (Prostar 230) and with a diode array detector (Prostar 330). An MeOH-(water 0.1% formic acid ($HCO_2H$)) mixture is used as elution solvent, at a flow rate of 1 ml/min, according to a linear gradient starting from 20% up to 47% MeOH over the course of 13.5 minutes, and then maintaining 47% MeOH for 10 minutes and, finally, from 47% to 100% MeOH over the course of 10 minutes. The fractions are visualized at a wavelength of between 200 nm and 400 nm.

A weight of 178 mg of fraction A and a weight of 39.5 mg of fraction B are collected.

Example 2.2

Isolation of the Compounds of Formula (I)

The two fractions A and B selected in example 2.1 are used to purify the compounds of the invention and to carry out the quantification thereof in each of the fractions of example 2.1.

The isolation of the compounds of formula (I) (VT1, VT2 and VT3) from each of the two fractions selected is carried out by semi-preparative HPLC, using a Gilson chromatograph equipped with a gradient pump (Gilson 322), with a UV detector (Gilson UV-VIS 151) and with a Nucleodur C18ec column (5 μm, 250 mm×21 mm i.d.). Each fraction is prepared at 30 mg/ml in MeOH and then filtered (Minisart RC 15 filters, 0.45 μm). The elution conditions call for an MeOH-(water+0.1% $HCO_2H$) mixture under the following conditions: from 20% to 47% MeOH over the course of 13.5 minutes, 47% MeOH for 10 minutes, and a return to 20% over the course of 5 minutes, at the flow rate of 14 ml/min. The detection is carried out at 205 nm.

After purification of fraction A by semi-preparative HPLC, a weight of 64 mg of the VT1 compound and a weight of 112 mg of the VT2 compound are collected.

After purification of fraction B according to the same method, a weight of 20 mg of the VT3 compound is collected.

The contents of each of the VT1, VT2 and VT3 compounds and the cumulative (VT1+VT2+VT3) content in each of the fractions A and B and in the fraction (A+B) are indicated in table 2 below.

TABLE 2

|  | VT1 | VT2 | VT3 | VT1 + VT2 + VT3 |
|---|---|---|---|---|
| % VT in fraction A + B |  |  |  | 90.00 |
| % VT in fraction A | 35.00 | 63.00 | — | 98.00 |
| % VT in fraction B | — | — | 51.00 | 51.00 |

Conclusions

Fractions A and B each constitute an extract specifically enriched in compounds of formula (I) which constitutes a subject of the invention, since each one consists of more than 50% by weight of compounds of formula (I).

These two fractions can also be combined into a single fraction (A+B) which also constitutes an example of a specifically enriched extract of the invention. This combination makes it possible to obtain an extract comprising each of the three compounds identified (VT1, VT2 and VT3), the whole being at a content of 90% by weight in the dry extract.

Each of these extracts can thus be used as a cosmetic or dermatological active agent in cosmetic or dermatological compositions.

Example 3

Structural Elucidation of the Compounds of Formula (I)

The structural elucidation of the compounds of formula (I) extracted from the PM of the orchid *Papilionanthe teres* (example 1.2), and then isolated by size fractionation and RP-HPLC, calls for a collection of spectral techniques.

Material

Mass Spectrometry (MS)

The vandaterosides are analyzed by high performance liquid chromatography on an Agilent 1200 RRLC, equipped with a Supelco Discovery $C_{18}$ column (25 cm×2.1 mm i.d.×5 μm) and coupled to an Agilent 6520 Accurate Mass QTOF mass spectrometer equipped with an ESI source.

The elution conditions call for an acetonitrile (ACN)–(water+0.01% $HCO_2H$) mixture under the following conditions: from 2% to 50% ACN over the course of 30 minutes, then change to 95% ACN over the course of 5 minutes, maintaining at 95% ACN for 5 minutes, and return to 2% ACN over the course of 5 minutes, with a flow rate of 0.6 ml/min.

Moreover, the ESI MS high-resolution mass spectra were obtained on a Bruker microToF-Q spectrometer with an ESI positive source. The calibrations were carried out using a $10^{-4}$ M solution of Li formate in an isopropanol/water mixture (50/50 v/v).

Nuclear Magnetic Resonance (NMR)

The NMR analyses were carried out on a Bruker 400 MHz Avance III spectrometer. It is necessary to obtain 1D ($^1H$ and $^{13}C$) and 2D (Cosy, HSQC, HMBC) spectra for complete structural elucidation of the molecules isolated. The spectra are analyzed on NMR Notebook software.

A minimum of 10 mg of the purified molecules is diluted in 600 μl of deuterated DMSO (DMSO $D_6$, $C_2D_6OS$; 99.9% D, Sigma). The minimum concentration thus obtained is in the region of 16 mg/ml.

Ultraviolet (UV) Spectrometry:

The UV spectra characteristic of the vandaterosides are obtained using a Shimazu UV-2401PC apparatus. The molecules are dissolved in MeOH at $5.10^{-5}$ M for VT1 and $2.5.10^{-5}$ M for VT2 and VT3. The molar extinction coefficient $\xi$ ($mol^{-1} \cdot L \cdot cm^{-1}$) is determined according to the Beer-Lambert law:

$$A = \xi \times c \times l$$

A=Absorbance of the molecule at a wavelength λ
C=concentration of the molecule (in mol/L)
l=length of the optical path (in cm)

Polarimetry

The determination of specific optical rotation [α] of polarized light by the asymmetric carbon of the vandaterosides is carried out on a Perkin Elmer 341 polarimeter. The molecules are kept in solutions at 1 mg/ml in MeOH and placed in the measuring cell of the polarimeter in order to measure the angle of rotation of polarized light at 589 nm and 20° C. $[\alpha]^{20°}$ of each of the molecules is thus determined according to Biot's law:

$$\alpha = [\alpha]^{T°} \times l \times c$$

α=angle of rotation observed (in degrees)=
l=length of the cuvette (in dm)
c=concentration of the solution (in g/ml)
$[\alpha]^{T°}$=specific optical rotation defined at a temperature T and measured for a given wavelength (expressed in $g^{-1} \cdot mL \cdot dm^{-1}$)

Structural Elucidation Results

The data of the NMR spectrum obtained for each of the VT1, VT2 and VT3 compounds are indicated in table 3 below:

TABLE 3

| No. | VT1 $^{13}C$ | VT1 $^1H$ (J in Hz) | VT2 $^{13}C$ | VT2 $^1H$ (J in Hz) | VT3 $^{13}C$ | VT3 $^1H$ (J in Hz) |
|---|---|---|---|---|---|---|
| 1 | 173.73 | | 173.42 | | 170.00 | |
| 2 | 75.30 | | 75.31 | | 80.36 | |
| 3 | 42.45 | 2.41 (d: 16.0) | 42.35 | 2.48 (d: 16.7) | 39.51 | 2.95 (d: 17.7) |
| | | 2.74 (d: 16.0) | | 2.84 (d: 16.7) | | 2.81 (d: 17.7) |
| 4 | 171.64 | | 169.42 | | 169.00 | |
| 5 | 43.64 | 2.77 (m) | 43.53 | 2.81(m) | 40.82 | 2.99 (m) |
| | | | | | | 3.01 (m) |
| 6 | 125.70 | | 125.43 | | 125.34 | 6.21 (d: 2.5) |
| 7, 11 | 131.50 | 6.90 (d: 8.5) | 131.17 | 6.91 (d: 8.5) | 131.47 | 6.96 (d: 8.5) |
| 8, 10 | 114.91 | 6.59 (d: 8.5) | 114.48 | 6.60 (d: 8.5) | 114.43 | 6.58 (d: 8.5) |
| 9 | 155.96 | | 155.90 | | 156.11 | |
| 1' | 129.14 | | 128.98 | | 130.35 | |
| 7' | 65.85 | 4.98 | 65.15 | 4.96 | 65.58 | 4.93 (d: 5) |
| | | | | | | 4.97 (d: 5) |
| 2', 6' | 129.40 | 7.22 (d: 8.5) | 129.44 | 7.25 (d: 8.6) | 129.71 | 7.27 (d: 8.4) |
| 5', 3' | 116.20 | 6.98 (d: 8.5) | 115.96 | 7.01 (d: 8.6) | 116.06 | 7.03 (d: 8.4) |
| 4' | 157.53 | | 157.08 | | 157.31 | |
| 4'O-Glc-1 | 100.54 | 4.84 (d: 7.0) β | 100.17 | 4.86 (d: 6.8) β | 100.06 | 4.88 (d: 7.2) β |
| 2 | 73.12 | 3.23 (m) | 73.05 | 3.23 (m) | 73.22 | 3.23 (m) |
| 3 | 77.00 | 3.35 (m) | 76.84 | 3.30 (m) | 76.59 | 3.28 (m) |
| 4 | 69.74 | 3.15 (m) | 69.53 | 3.15 (m) | 69.67 | 3.15 (m) |
| 5 | 76.60 | 3.28 (m) | 76.44 | 3.28 (m) | 76.98 | 3.33(m) |
| 6 | 60.70 | 3.68 (dd: 1.5/12.5) | 60.52 | 3.68 (dd: 4.9/11) | 60.66 | 3.69 (dd: 1.7/11.7) |
| | | 3.45 (dd: 6.1/12.5) | | 3.46 (dd: 5.3/11) | | 3.47 (dd: 6.8/11.7) |
| 4''-O-Glc-1 | | | 100.17 | 4.84 (d: 6.8) β | 100.12 | 4.87 (d: 7.2) β |
| 2 | | | 73.05 | 3.23 (m) | 73.22 | 3.23 (m) |
| 3 | | | 76.84 | 3.30 (m) | 76.59 | 3.28 (m) |
| 4 | | | 69.53 | 3.15 (m) | 69.67 | 3.15 (m) |
| 5 | | | 76.44 | 3.28 (m) | 76.98 | 3.33(m) |
| 6 | | | 60.52 | 3.68 (dd: 4.9/11) | 60.66 | 3.69 (dd: 1.7/11.7) |
| | | | | 3.46 (dd: 5.3/11) | | 3.47 (dd: 6.8/11.7) |
| 1'' | | | 128.86 | | 128.71 | |
| 7'' | | | 65.63 | 4.96 | 66.23 | 5.01 (d: 6.6) |
| 2'', 6'' | | | 129.40 | 7.22 (d: 8.6) | 129.64 | 7.27 (d: 8.4) |
| 5'', 3'' | | | 115.90 | 7.00 (d: 8.6) | 116.16 | 7.03 (d: 8.4) |

TABLE 3-continued

| No. | VT1 $^{13}$C | VT1 $^{1}$H (J in Hz) | VT2 $^{13}$C | VT2 $^{1}$H (J in Hz) | VT3 $^{13}$C | VT3 $^{1}$H (J in Hz) |
|---|---|---|---|---|---|---|
| 4″ | | | 157.08 | | 157.34 | |
| 3-O-Glc-1 | | | | | 98.04 | 4.82 (d: 7.8) B |
| 2 | | | | | 71.60 | 3.26(m) |
| 3 | | | | | 77.98 | 4.92 (dd: 9.5/9.5) |
| 4 | | | | | 67.44 | 3.39(m) |
| 5 | | | | | 76.50 | 3.10(m) |
| 6 | | | | | 60.28 | 3.49 (dd: 4.5/11.8) |
| | | | | | | 3.68 (dd: 1.7/11.8) |
| Cin-1 | | | | | 165.71 | |
| Cin-2 | | | | | 118.42 | 6.67 (d: 15.7) |
| Cin-3 | | | | | 144.19 | 7.68 (d: 15.7) |
| Cin-4 | | | | | 134.17 | |
| Cin-5, 9 | | | | | 128.26 | 7.74 (dd: 2.8/6.8) |
| Cin-6, 8 | | | | | 128.94 | 7.44 (m) |
| Cin-7 | | | | | 128.67 | 7.44(m) |

Table 3: NMR spectrum ($^{1}$H: 400 MHz, $^{13}$C: 100 MHz, DMSO D$_6$, δ in ppm, J in Hz) obtained for each of the VT1, VT2 and VT3 compounds.

The results obtained for the various analytical methods used are detailed below for each compound.

VT1

Appearance: yellow-colored resin

Solubility: soluble in MeOH and DMSO, low solubility in water

Figure 3:
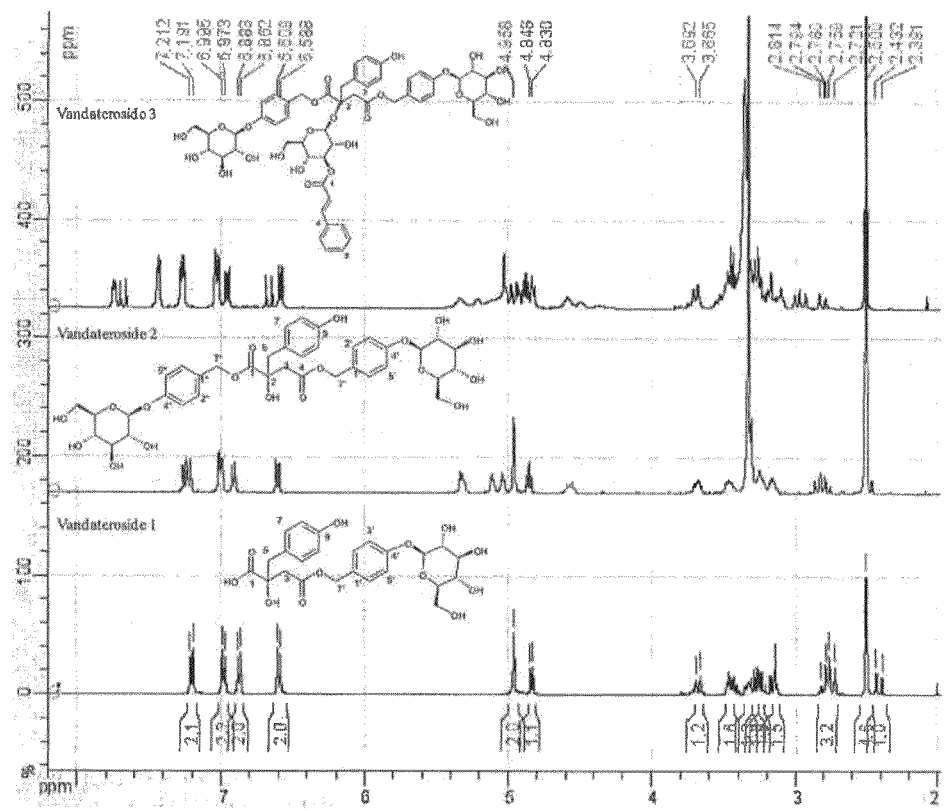
FIG. 3 represents the $^1$H NMR spectra of the VT1, VT2 and VT3 compounds of the invention.
Figure 4:
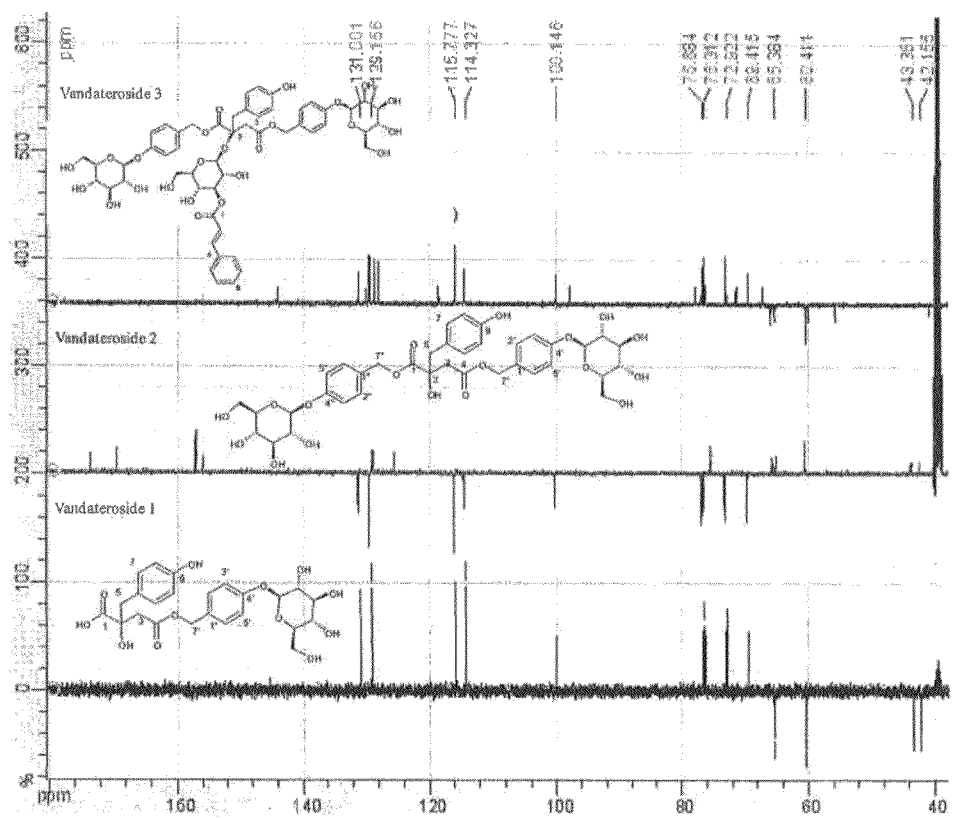
FIG. 4 represents the $^{13}$C NMR spectra (DEPT135) of the VT1, VT2 and VT3 compounds of the invention.

NMR: $^{1}$H NMR and $^{13}$C NMR data (DMSO D$_6$, 400 MHz and 100 MHz)→FIGS. 3 to 4 and table 3.

MS: HR-ESI-MS ion [(M+NH$_4$)]$^+$ at m/z=526.19236 (molecular formula calculated for $C_{24}H_{28}O_{12}$: 508.15808 Δ: −0.89 ppm).→FIG. 2 and table 4

TABLE 4

Peak List

| m/z | z | Abund | Formula | Ion |
|---|---|---|---|---|
| 526.19236 | 1 | 734161 | C24 H32 N O12 | (M + NH4)+ |
| 527.19494 | 1 | 168021 | C24 H32 N O12 | (M + NH4)+ |

Formula Calculator Results

| Formula | Best | Mass | Tgt Mass | Diff (ppm) | Ion Species | Score |
|---|---|---|---|---|---|---|
| C24 H28 O12 | TRUE | 508.15853 | 508.15808 | −0.89 | C24 H32 N O12 | 95.88 |

Figure 5:
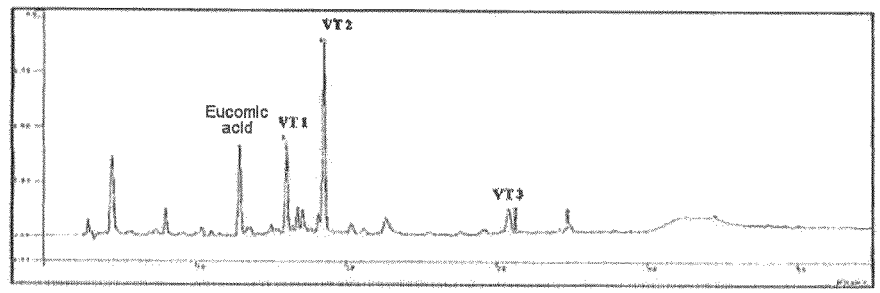
FIG. 5 represents the profile obtained by HPLC and UV detection of the extract according to Example 1.2 (solubilized in 5 mg/mL MeOH) comprising the VT1, VT2 and VT3 compounds of the invention.

UV: absorption maxima at 203 (log ξ 4.2), 225 (log ξ 4.0) and 278 (log ξ 3.2) nm.→FIG. 5

$[α]_{MeOH}^{20°}=−50°$ g$^{-1}$·mL·dm$^{-1}$

Acid Hydrolysis

After acid hydrolysis of the molecules (3 h at 80° C., in the presence of 2.0 M HCl), the aqueous phase is washed 3 times using n-butanol saturated with water, and then evaporated to dryness. A mixture (1:4, v/v) of pyridine and 1-(trimethylsilyl)imidazole (Sigma) is added to the dry residue and then heated for 1 hour at 60° C. in order to carry out a derivation. 1 to 2 μl of the reaction mixture are then diluted in 500 μl of analytical CH$_2$Cl$_2$ and then analyzed using a gas chromatograph (of the Trace GS Ultra type) equipped with a TR-5MS SQC capillary column (15 m×0.25 mm*0.25 μm) and coupled to a mass spectrometer (Thermo Scientific DSQII). Detection is obtained by electron impact at 70 eV. The conditions used are the following: 1 minute at 40° C. then a gradient of 10° C./min up to 250° C. and maintaining of a stationary phase at 250° C. (helium flow rate 1 ml/min, injector temperature 250° C., transfer line temperature 285° C.). The detection is carried out after 2 minutes of analysis, the mass measurement interval is spread from 0 to 500.

The sugar released at the end of the add hydrolysis is identified by comparison with the retention time and mass spectrum of the D-glucose control (Merck) (Tr=15.60 minutes) having undergone the same derivation process. For the three vandaterosides analyzed, the sugar identified after hydrolysis is O-glucose,

VT2

Appearance: amorphous white powder

Solubility: in water, formation of a gel at approximately 10 mM. VT 2 is soluble in MeOH and in DMSO, low solubility in water.

NMR: $^{1}$H NMR and $^{13}$C NMR data (DMSO D$_6$, 400 MHz and 100 MHz)→FIGS. 3 to 4 and table 3.

MS: HR-ESI-MS ion [(M+NH$_4$)]$^+$ at m/z=794.28867 (molecular formula calculated for $C_{38}H_{44}O_{18}$: 776.25276 Δ: −0.01 ppm).→FIG. 2 and table 5

TABLE 5

Peak List

| m/z | z | Abund | Formula | Ion |
|---|---|---|---|---|
| 213.09124 | | 35369 | | |
| 359.11334 | | 139175 | | |
| 453.15531 | 1 | 145631 | | |
| 454.15825 | 1 | 36147 | | |
| 465.15525 | | 43977 | | |
| 794.28867 | 1 | 618328 | C37 H48 N O18 | (M + NH4)+ |
| 795.29123 | 1 | 229976 | C37 H48 N O18 | (M + NH4)+ |
| 796.29232 | 1 | 58672 | C37 H48 N O18 | (M + NH4)+ |
| 799.242 | | 31867 | C37 H44 Na O18 | (M + Na)+ |

Formula Calculator Results

| Formula | Best | Mass | Tgt Mass | Diff (ppm) | Ion Species | Score |
|---|---|---|---|---|---|---|
| C37 H44 O18 | TRUE | 776.25277 | 776.25276 | −0.01 | C37 H44 Na O18 | 98.6 |

UV: absorption maxima at 203 (log $\xi$ 4.5) 225 nm (log $\xi$ 4.5) and 278 (log $\xi$ 3.5) nm.→FIG. 5

$[\alpha]_{MeOH}^{20°} -56°\text{g}^{-1}\cdot\text{mL}\cdot\text{dm}^{-1}$

Acid hydrolysis: refer to VT1 VT3

Appearance: yellow-colored resin

Solubility: compound soluble in MeOH and DMSO, low solubility in water.

NMR: $^1$H NMR and $^{13}$C NMR data (DMSO $D_6$, 400 MHz and 100 MHz)→FIGS. 3 to 4 and table 3.

Figure 1:
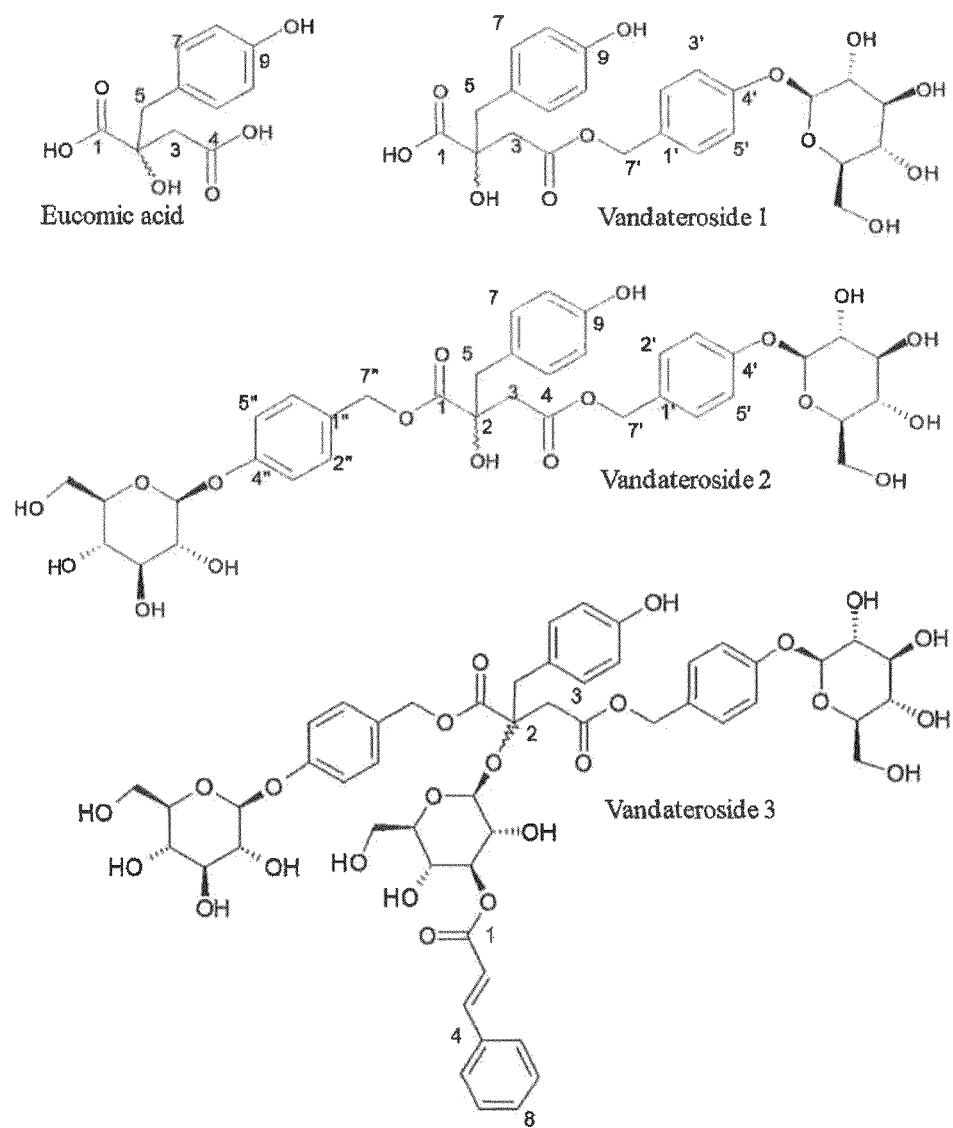
FIG. 1 represents the semi-structural formulae of the VT1, VT2 and VT3 compounds of the invention and also of eucomic acid.
Figure 2:
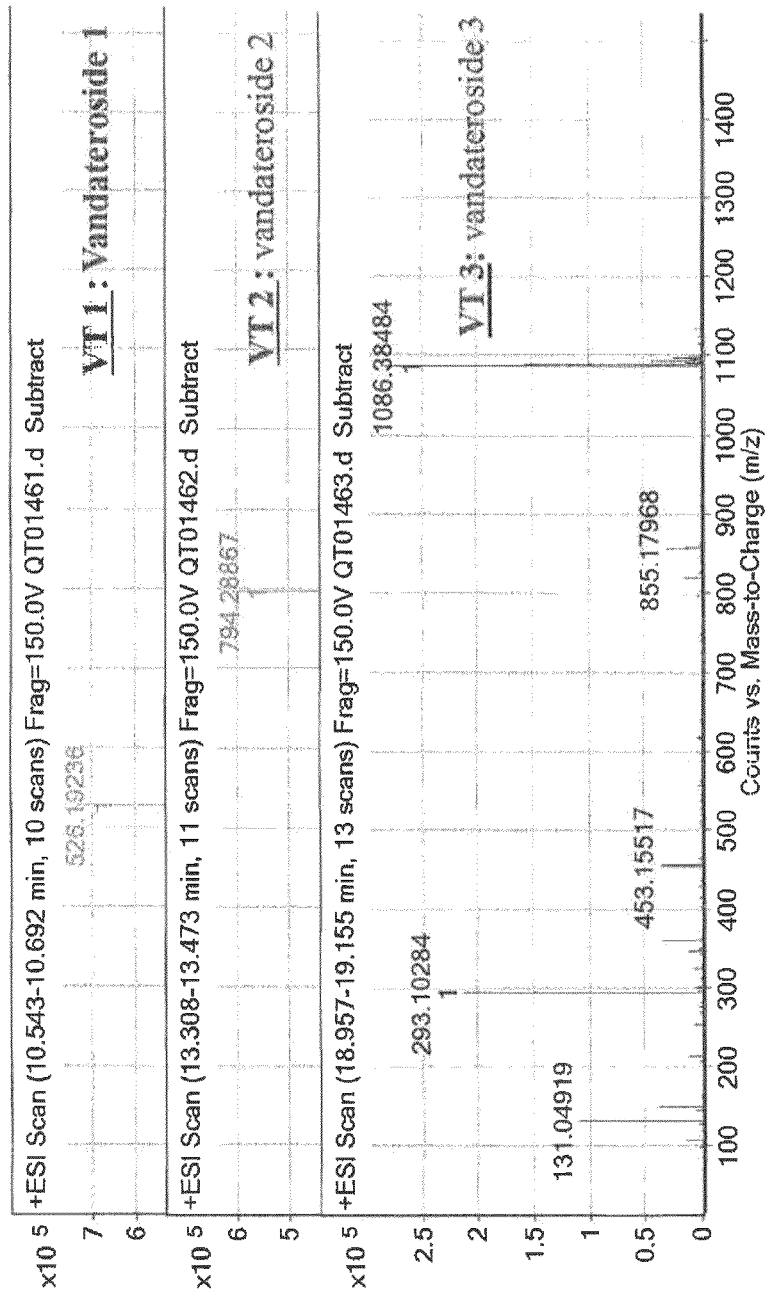
FIG. 2 represents the mass spectra of the VT1, VT2 and VT3 compounds of the invention.

MS: HR-ESI-MS ion $[(M+NH_4)]^+$ at m/z=1086.38484 (molecular formula calculated for $C_{52}H_{60}O_{24}$: 106834745 Δ: −1.89 ppm). FIG. 2 and table 6

TABLE 6

Peak List

| m/z | z | Abund | Formula | Ion |
|---|---|---|---|---|
| 107.04922 | | 15338 | | |
| 131.04919 | | 111862 | | |
| 149.05972 | | 39325 | | |
| 293.10284 | 1 | 220337 | | |
| 294.10592 | 1 | 33624 | | |
| 359.11327 | | 35374 | | |
| 453.15517 | | 36506 | | |
| 455.15568 | | 34663 | | |
| 818.28701 | | 16049 | | |
| 855.17968 | | 30955 | | |
| 1086.38484 | 1 | 287785 | C52 H64 N O24 | (M + NH4)+ |
| 1087.38772 | 1 | 157791 | C52 H64 N O24 | (M + NH4)+ |
| 1088.38858 | 1 | 54091 | C52 H64 N O24 | (M + NH4)+ |
| 1091.33884 | 1 | 44018 | C52 H60 Na O24 | (M + Na)+ |
| 1092.34148 | 1 | 25636 | C52 H60 Na O24 | (M + Na)+ |
| 1096.31521 | 2 | 21723 | | |
| 1096.81644 | 2 | 24710 | | |
| 1097.31801 | 2 | 19284 | | |

Formula Calculator Results

| Formula | Best | Mass | Tgt Mass | Diff (ppm) | Ion Species | Score |
|---|---|---|---|---|---|---|
| C52 H60 O24 | TRUE | 1058.34948 | 1068.34745 | −1.89 | C52 H60 Na O24 | 96.2 |

UV: absorption maxima observed at 223 (log ξ 4.5) nm and 276 (log ξ 3.5) nm.→FIG. 5
$[\alpha]_{MeOH}^{20\,°} = -37°g^{-1}$ mL·dm$^{-1}$
Acid hydrolysis: refer to VT1

Example 4

Biological Activity of the Compounds of the Invention

Treatments

A stock solution of each of the three compounds previously isolated, VT1, VT2 and VT3, is prepared in DMSO (Sigma).

The stock solutions are then diluted directly in the culture medium, with a view to treatment of the cells (normal human keratinocytes NHKs or HaCaT cell line).

Stimulation of Mitochondrial Dehydrogenases on Keratinocytes

Normal human keratinocytes (NHKs), isolated from eyelids of 37-year-old Caucasian women, are cultured at passage 3 in complemented (Invitrogen) Keratinocyte Serum Free Medium (KSFM, Invitrogen) supplemented with 5% of fetal calf serum (FCS, Invitrogen).

The NHKs are seeded in 96-well plates (Greiner Bio One) in a proportion of $1.10^4$ cells/well, and then incubated at 37° C., 5% $CO_2$ for 24 h. These cells are then treated, after $UV_B$ irradiation (60 mJ/cm$^2$ Vilbeit-Lourmat irradiator) or without irradiation, with serial dilutions of the VT1, VT2 and VT3 compounds (from 6.25 to 0.78 μg/ml) diluted in DMSO (sigma) 0.1% v/v final concentration. The plates are incubated at 37° C., 5% $CO_2$. The untreated cells containing 0.1% v/v of DMSO are considered to be a negative control. After treatment for 48 h, the supernatants are removed and the XTT solution (Cell proliferation kit II, Roche Diagnostic) is deposited in each well in order to determine the overall activity of the mitochondrial dehydrogenases. This activity is evaluated by means of the conversion of an XTT tetrazolium salt to soluble formazan, via a cell mechanism which calls for the enzymatic activities of the glycolytic NAD(P)H dehydrogenase (complex I) and of succinate dehydrogenase (complex II), which are constituents of the mitochondrial respiratory chain. The amount of colored formazan (determined by reading optical density at 450 nm) is directly related, firstly, to the enzymatic activity of the mitochondrial dehydrogenases and, secondly, to the amount of metabolically active cells (Roehm et al. *J. Immunol. Methods*, 1991; 142: 257-265). After incubation for 3 hours, the XTT is reduced to a soluble formazan by the dehydrogenases. The 96-well plates are read at 450 nm with a spectrofluorometer (SpectraFluor Plus, Tecan). The total proteins are assayed in each well by means of the BCA technique (Bicinchoninic acid assay (Uptima Interchim kit)).

The results are expressed as mean of the optical densities (OD) at 450 nm and standardized relative to the total concentration of cell proteins (expressed in μg/ml), which makes it possible to measure only the activity of the dehydrogenases and to dispel with the impact of cell proliferation on the measurement of the ODs obtained.

The mean results obtained for each concentration of molecules (Rm) are compared with those obtained for the negative control (Rc):

Rm/Rc>1 indicates a stimulation of the mitochondrial dehydrogenase activity.

Stimulation of Cytochrome C Oxidase on Modified Human Keratinocytes (HaCat)

The objective of the study is to evaluate the potential of the compounds which are the subject of the invention for stimulating the performance levels of the mitochondrial respiratory chain. The assays are carried out on genetically modified human keratinocytes (HaCaT).

The HaCaT cells were cultured in 6-well plates in RPMI 1640 medium (Roswell Park Memorial Institute) w/o HEPES (Invitrogen) supplemented with 10% of fetal calf serum (FCS, Invitrogen) and a penicillin/streptomycin mixture, until confluence. They were then treated, in DMEM (Dulbecco's Modified Eagle Medium, Invitrogen) containing 4.5 g/L of glucose, 0.1% BSA (Bovine Serum albumin AM2618 Invitrogen), with serial dilutions of vandaterosides (from 6.25 to 0.78 μg/ml) diluted in DMSO (0.1% v/v final concentration). Resveratrol (Sigma) at 50 μM, i.e. 11.41 μg/ml, was used as positive reference. The untreated cells containing 0.1% v/v of DMSO were considered to be a negative control. After treatment for 3 h, the cells were lysed (20 mM HEPES, 0.1% Triton, 1 mM EDTA) and the total cell proteins were assayed by means of the Bradford technique (B6916 Sigma). The total protein concentration of each sample was then adjusted to 2 mg/ml.

The cell lysate was incubated in the presence of an assay buffer (Sigma) in order to determine the enzymatic kinetics without the addition of substrate, denoted Vo. Cytochrome C (from equine heart C-7752 Sigma) reduced with DTT (dithiothreitol, Sigma) was added to the assay buffer at 50 μM in order to measure the rate of the enzymatic reaction. The disappearance of the reduced cytochrome C was monitored using a spectrophotometer [Beckman DU 640] at 550 nm for 90 seconds according to the manufacturer's (Sigma) instructions. The results were calculated from the enzymatic kinetics curves and are expressed as cytochrome C oxidase activity (U/μg of proteins).

The equations allowing the calculation of the enzymatic activities are the following:

Enzymatic activity of cytochrome $C$ in U/ml=$A_{COX}$= $(DA/\text{min})/21.84$ with:
DA/min=A/min(v)−A/min (v0)
21.84 (mM)=ϵ(molar extinction coefficient) of ferrocytochrome C at 550 nm
A=Absorbance at 550 nm
A/min(v)=Absorbance at 550 nm at time "v" in minutes, corresponding to the time of the measurement after the addition of the substrate;
A/min (v0)=Absorbance at 550 nm at time "v0" (at the start, i.e. before the addition of substrate) in minutes.

The results are expressed by comparison of the enzymatic activity measured in the presence of the vandaterosides ($A_{COX}$ samples) relative to the control enzymatic activity ($A_{COX}$ control): i.e. ($A_{COX}$ samples)/($A_{COX}$ control).

A calculated ($A_{COX}$ samples)/($A_{COX}$ control) ratio of greater than 1 indicates stimulation of the activity of cytochrome C oxidase in the presence of the samples.

Measurement of Mitochondrial Biogenesis on Modified Human Keratinocytes (HaCaT)

For the vandaterosides VT1 and VT2, which showed a stimulatory effect on the activity of cytochrome C, mitochondrial biogenesis measurements are carried out.

The objective is to verify whether or not the increase in enzymatic activity measured is linked to a basal stimulation of the respiratory chain of the mitochondria initially present or to an increase in the number of intracellular mitochondria, indicative of a stimulation of mitochondrial biogenesis.

The HaCaT cells are cultured in 6-well plates and then treated as described above. After treatment for 48 h, the cells are lysed with a buffer consisting of 10 mM of Tris base, 1 mM EDTA, 0.3M of sodium acetate and 1% SDS (1 ml/well)

and according to an incubation time of overnight at 55° C. The mitochondrial DNA is extracted from the cell lysate with a phenol solution (1/1 ratio). Two cycles of centrifugation at 4000 rpm (5 minutes) are carried out. A solution de $CHCl_3$/isoamyl alcohol (24:1, v/v) is then added to the upper aqueous phase, recovered after settling out. The mixture is then centrifuged (5 minutes, 4000 rpm, 4° C.).

Precipitation of the total DNA is induced by adding an absolute ethanol/3M sodium acetate mixture ($2.5/1.10^e$, v/v) to the supernatant. After centrifugation (30 minutes, 12000 rpm, 4° C.), the pellets are washed with EtOH at 70° v/v, and then dried and taken up in deionized water. The DNA is assayed using a spectrometer (Thermo Scientific Nanodrop). The DNA solutions are adjusted to a concentration of 10 ng/μl.

The expression of three different genes is measured by qPCR. This technique makes it possible to measure the amount of DNA polymerized by means of a fluorescent label. The genes selected are two mitochondrial genes, 16S and COX2, corresponding respectively to the genes for expression of a mitochondrial ribosome and of cytochrome C oxidase, and also a gene, UCP-2, located in the cell nucleus (genomic DNA). Measurement of the expression of this gene serves as a control.

The primers used are the following:

```
16S DNA:
sense
(5'-TGG-ACA-ACC-AGC-TAT-CAC-CA-3')
and
antisense
(5'-ACT-TTG-CAA-GGA-GAG-CCA-AA-3');

COX-2 DNA:
sense
(5'-AGG-CGA-CCT-GCG-ACT-CCT-TGA-3')
and
antisense
(5'-TTA-GCT-TTA-CAG-TGG-GCT-CTA-GAG-GC-3');

UCP-2 DNA:
sense
(5'-CCT-AGC-GCT-GCC-TCA-TAA-AC-3')
and
antisense
(5'-CCT-ATG-GGT-CTG-TGC-CTG-TT-3').
```

The qPCR experiments are carried out in 96-well plates. A range of DNA, corresponding to the mixture of DNA of all the samples, is prepared according to a serial dilution, for each primer. The cellular DNA samples are mixed with a mixture of MIX-PCR SYBR Green (Applied Biosystems), to which deionized water is added, 45 PCR cycles are carried out with a hybridization temperature of 60° C. (StepOnePlus Thermocycler, Applied Biosystems).

The fluorescence is measured after the 45 cycles and the amount of DNA obtained is determined by means of the DNA range.

The results are expressed in amount of 16S and COX2 ($Q_{COX2}$) DNA, calculated according to the amount of UCP-2 genomic DNA ($Q_{UCP-2}$), and which is defined as ($Q_{COX2}$)/($Q_{UCP-2}$)

A calculated ($Q_{COX2}$)/($Q_{UCP-2}$) ratio of greater than 1 indicates an increase in the amount of mitochondrial DNA, and reflects an increase in the number of intracellular mitochondria.

Results

The XTT measurements after 48 h of treatment show that the compounds tested significantly stimulate the mitochondrial respiratory functions of the keratinocytes. No significant dose effect is, however, observed.

Moreover, after $UV_B$-irradiation of the keratinocytes, no significant stimulation of the dehydrogenases is observed.

The VT1 and VT2 compounds are the compounds which most effectively stimulate the activity of the keratinocyte mitochondrial dehydrogenases.

In particular, the VT2 compound significantly stimulates the activity of the dehydrogenases at the lowest tested concentration of 0.78 μg/ml, i.e. 1 μM (+39% relative to the negative control) (FIG. 6).

The three compounds tested activate cytochrome C oxidase, at lower concentration levels than resveratrol (positive control), the VT2 compound being the best cytochrome C oxidase activator. At a concentration of 1.56 μg/ml (2 μM), VT2 stimulates cytochrome C oxidase activity at a level of activity comparable to resveratrol at the concentration of 11.41 μg/ml (50 μM) (FIG. 7).

A dose effect is observed only for the VT1 compound.

For VT1 and VT2, a mitochondrial biogenesis measurement is carried out in order to determine whether the increase in enzymatic activity measured is linked to a basal stimulation of the respiratory chain of the mitochondria initially present, or to an increase in the number of intracellular mitochondria.

The results indicate that, at the concentrations tested, with the exception of VT1 at 6.25 μg/ml, neither of the two compounds induces an activation of mitochondrial biogenesis, and therefore an increase in the number of intracellular mitochondria.

Consequently, the results obtained, which demonstrate an increase in the enzymatic activity of mitochondrial cytochrome C oxidase or dehydrogenases, reflect a basal stimulation of these enzymatic activities and not an increase in the number of intracellular mitochondria.

VT1 and VT2 exhibit the best potential for mitochondrial activation, by means of a stimulation of the enzymatic activity of the dehydrogenases of complexes I and II, and via stimulation of cytochrome C oxidase of the mitochondrial respiratory chain.

The VT1 and more particularly VT2 compounds therefore each exhibit a significant activity with respect to the mitochondrial respiratory chain of keratinocytes, via stimulation of complexes I and II of said chain and stimulation of cytochrome C oxidase activity. This confirms that they activate the energy metabolism of the skin cell by means of its mitochondrial respiratory functions.

This activity justifies the use of the compounds of the invention, in particular VT1 and/or VT2, as cosmetic or dermatological active agents, and more particularly for the cosmetic or dermatological treatment of mature skin, such as combating skin aging and/or maintaining or improving skin moisturization and/or skin healing.

Stimulation of the Differentiation of Normal Human Keratinocytes (NHKs)

Desmogleins are cadherins, transmembrane proteins, which bind epithelial cells, such as keratinocytes, to one another by means of the formation of desmosomes. Just like loricrin, involucrin is a protein expressed by the constituent keratinocytes of the horny layer which have reached the terminal differentiation stage. These keratinocytes are called corneocytes. Transglutaminases, which are $Ca^{2+}$-dependent enzymes, carry out the formation of covalent points between these proteins. These three types of proteins therefore constitute markers for early differentiation (desmoglein I) and late differentiation (involucrin and transglutaminases) of keratinocytes. A slowing down of the renewal of keratinocytes, of their activity and of their transformation into corneocytes is observed during skin aging. Atrophy of the epidermis is observed. The skin dehydrates, and the protective and healing functions of the epidermis are then slowed down. The skin then takes on a lifeless and dried-out appearance.

Method

The NHKs are cultured at passage 3 in complete KSFM medium in a T75 flask. At the pre-confluence stage, the NHKs are trypsinized and seeded in a proportion of 20 000 cells per well in 8-well Lab-Tek II culture systems (Nalge Nunc International), 4 wells per treatment condition. At 80% confluence, the cells are treated for 5 days with the various compositions of active agents (VT1, VT2, VT3, each at 12 μg/ml) until the post-confluence stage is reached. Vitactyl® clair (extract of *Malva sylvestris*, Silab) at 3% is used as a positive control.

Immunolabeling

The cells are rinsed with PBS (PBS Tablets, Invitrogen GIBCO) and then fixed with formalin (Formalin Solution, 10%, Neutral Buffered, Sigma) for 10 minutes.

After rinsing with PBS, the culture chambers are filled with a 0.1% Triton solution (Triton X-100, Sigma) for 10 minutes in order to permeabilize the membranes, and then rinsed twice with PBS. The cells are then covered with a solution of PBS/1% BSA (BSA, Sigma) for 30 minutes at ambient temperature. The PBS/BSA solution is removed from the slides by inclining them on absorbent paper.

The cells are then covered with a solution of prim antibodies for 60 minutes at ambient temperature:
- anti-transglutaminase (Mouse monoclonal, Harbor Bio product) diluted to 1/200,
- anti-desmoglein 1 (Mouse monoclonal—Zymed) diluted to 1/100;
- anti-involucrin (Mouse monoclonal—Neomarkers) diluted to 1/200.

After rinsing with PBS, the cells are then covered with a solution of secondary antibody diluted to 1/200 (Alexa fluor 488, goat anti-mouse IgG (Molecular probes)). The slides are incubated for 60 minutes at ambient temperature, in the dark. The slides are rinsed three times in PBS.

Mounting

The culture chamber of the slides is taken off and a few drops of mounting medium (Fluorescent Mounting Medium, DAKO) are deposited on the cells and then covered with a coverslip (24×60 mm, Knittel Glaeser).

Acquisition of Photographs by Confocal Microscopy

The images are taken on a videomicroscope (Nikon TE 2000) with an Alexa fluor. 488 filter.

For each condition, four photos are taken in green fluorescence (expression of the markers) with the ×20 objective. The acquisition parameter's (exposure time, gain) are identical for each marker studied.

The photos are analyzed using the Leica QWin image analysis software. A program is created in order to quantify the expression of these differentiation markers.

Results

The results show that the compounds of the invention significantly stimulate keratinocyte differentiation protein expression, compared with the negative control.

Among the compounds tested, VT1 and VT2 are the most effective (FIGS. 8 to 13). Moreover, VT2 stimulates involucrin expression at a level greater than that of the positive control used at 3%

This demonstrates that the vandaterosides, and more particularly VT1 and VT2, stimulate the renewal of the constituent keratinocytes of the upper layer of the epidermis.

The vandaterosides promote renewal of the stratum corneum, thus giving the skin a younger appearance. This phenomenon contributes to maintaining the protective and repair functions of the epidermis while at the same time maintaining or improving skin moisturization.

The invention claimed is:

1. A method for cosmetic care selected from the group consisting of: combating skin aging, for reducing or delaying the effects of skin aging, restructuring the epidermis, firming the skin, promoting the reduction or resorption of wrinkles and the protective properties of the epidermis, and for maintaining or improving skin moisturization and/or for promoting skin healing, said method comprising applying to the areas of skin that are involved a cosmetic composition in an amount effective for achieving the indicated effect, said cosmetic composition comprising a *Papilionanthe teres* extract comprising at least 40% by weight, relative to the total weight of the dry extract, of one or more compounds selected from the group consisting of 4-(4-β-D-glucopyranosyloxybenzyl)-(2R)-2-(p-hydroxybenzyl)-malate (VT1); 1,4-bis(4-β-D-glucopyranosyloxybenzyl)-(2R)-2-(p-hydroxybenzyl)-malate (VT2); and 1,4-bis(4-β-D-glucopyranosyloxybenzyl)-(2R)-2-(2-β-D-glucopyranosyl-3-trans-cinnamoyl ester)-2-(p-hydroxybenzyl)-malate (VT3).

2. The method of claim 1, wherein the extract comprises one or more compounds selected from the group consisting of: VT1 and VT2, at a cumulative content of greater than 40% by weight, relative to the weight of the dry extract.

3. The method of claim 1, wherein the extract comprises one or more compounds selected from the group consisting of: VT1 and VT2, at a cumulative content of greater than 60% by weight, relative to the weight of the dry extract.

4. The method of claim 1, wherein the extract comprises VT3 at a content of greater than 8% by weight, relative to the weight of the dry extract.

5. The method of claim 1, wherein the extract is made up of at least 80% by weight of VT1, VT2, and VT3, relative to the total weight of the dry extract.

* * * * *